(12) United States Patent
Okada et al.

(10) Patent No.: US 7,488,955 B2
(45) Date of Patent: Feb. 10, 2009

(54) MULTIPHOTON-EXCITATION OBSERVATION APPARATUS

(75) Inventors: Junichi Okada, Tokyo (JP); Makio Ueno, Nagano (JP); Yasunari Matsukawa, Saitama (JP)

(73) Assignee: Olympus Corporation, Tokyo (JP)

( * ) Notice: Subject to any disclaimer, the term of this patent is extended or adjusted under 35 U.S.C. 154(b) by 134 days.

(21) Appl. No.: 11/726,577

(22) Filed: Mar. 22, 2007

(65) Prior Publication Data
US 2007/0229946 A1 Oct. 4, 2007

(30) Foreign Application Priority Data
Mar. 28, 2006 (JP) .............................. 2006-088760

(51) Int. Cl.
*G02B 21/06* (2006.01)
(52) U.S. Cl. ................. 250/458.1; 250/459.1; 359/385
(58) Field of Classification Search .............. 250/458.1; 359/385
See application file for complete search history.

(56) References Cited

U.S. PATENT DOCUMENTS

| 5,796,112 A * | 8/1998 | Ichie ................. 250/458.1 |
| 7,329,880 B2 * | 2/2008 | Kubo .................. 250/458.1 |
| 2005/0157292 A1 * | 7/2005 | Saitoh et al. ............. 356/318 |

FOREIGN PATENT DOCUMENTS

| JP | 2847852 B2 | 11/1998 |
| JP | 2000-275541 A | 10/2000 |
| WO | WO 91/07651 A1 | 5/1991 |

OTHER PUBLICATIONS

Zipfel, W., "Nonlinear magic: multiphoton microscopy in the biosciences" Nature Biotechnology, vol. 21, No. 11, Nov. 2003, pp. 1369-1377, XP002444341 (p. 1375).
Wokosin, D., "All-Solid State Ultrafast Lasers Facilitate Multiphoton Excitation Fluorescence Imaging", IEEE Journal of Selected Topics in Quantum Electronics, vol. 2, No. 4, 1996, pp. 1051-1065, XP002444342, pp. 1058-1061.
So, Peter T., "Two-Photon Excitation Fluorescence Microscopy", Annu. Rev. Biomed. Eng., vol. 2, 2000, pp. 399-429, XP002444343, pp. 416 and 417.

* cited by examiner

*Primary Examiner*—David P Porta
*Assistant Examiner*—Djura Malevic
(74) *Attorney, Agent, or Firm*—Frishauf, Holtz, Goodman & Chick, P.C.

(57) ABSTRACT

The invention provides a multiphoton-excitation observation apparatus comprising a light-source unit for emitting pulsed laser light; an observation apparatus main unit for irradiating a specimen with laser light emitted from the light-source unit and observing fluorescence emitted from the specimen; an incidence adjusting device, disposed between the light-source unit and the observation apparatus main unit, for adjusting the beam diameter of the laser light emitted from the light-source unit; and a control apparatus for controlling the incidence-adjusting unit according to the depth of an observation plane in the specimen.

9 Claims, 7 Drawing Sheets

MULTIPHOTON-EXCITATION OBSERVATION APPARATUS

BACKGROUND OF THE INVENTION

1. Field of the Invention

This invention relates to multiphoton-excitation observation apparatuses.

This application is based on Japanese Patent Application No. 2006-088760, the content of which is incorporated herein by reference.

2. Description of Related Art

A multiphoton-excitation apparatus is a known apparatus in the related art for observing the function of cells and so forth by irradiating a biological specimen or the like with ultrashort pulsed laser light from the surface thereof and detecting the fluorescence emitted from the surface or the interior of the specimen due to multiphoton absorption (for example, see Publication of Japanese Patent No. 2848952).

Also known in the related art are scanning laser microscopes which acquire image data in a two-dimensional XY plane by detecting reflected light or transmitted light from a specimen while scanning a spot of light in the two-dimensional XY plane on the specimen, and which acquire image data at different depths in the specimen, ranging from a surface layer portion to a deep layer portion, by varying the focal position of the spot of light in the Z direction.

However, when the focal position is varied in the depth direction in this way, there is a phenomenon whereby the brightness decreases the deeper each acquired image becomes in the Z-direction. Conventionally, therefore, a technique for correcting the apparent brightness by subjecting the light level of the image data acquired in the observation to post-processing to obtain easily observed images with uniform brightness has been proposed (for example, see Japanese Unexamined Patent Application, Publication No. 2000-275541).

As biological research has progressed in recent years, there have been increasing demands for observing regions deeper inside biological specimens. A standard single-photon-excitation laser scanning microscope can acquire an optical internal tomogram of a specimen under observation by virtue of the confocal effect; however, the observable depth in the biological specimen is only about 50 µm from the surface.

A multiphoton excitation method described in Publication of Japanese Patent No. 2848952 excites fluorescence at near-infrared wavelengths, which have high transmittance through biological tissue and, therefore, are suitable for observing deep regions. However, even with multiphoton excitation, when observing a deep region exceeding a depth of 100 µm, for example, the effects of scattering, refraction, and absorption of the excitation light and the fluorescence by the specimen are strong, resulting in the problem that the resolution and S/N ratio decrease, which makes it impossible to acquire clear images.

BRIEF SUMMARY OF THE INVENTION

An object of the present invention is to provide a multiphoton-excitation observation apparatus which can acquire clear images from the surface layer portion to the deep layer portion, even when observing down to a very deep region (for example, to a depth of about 100 µm or more from the surface).

The present invention provides a multiphoton-excitation observation apparatus comprising a light-source unit; an observation apparatus main unit for irradiating a specimen with laser light emitted from the light-source unit and observing fluorescence emitted from the specimen; and a control apparatus. The light-source unit includes a pulsed laser light source for emitting pulsed laser light; and an incidence-adjusting unit for adjusting the beam diameter of the laser light emitted from the pulsed laser light source. The control apparatus controls the incidence-adjusting unit according to the depth of an observation plane in the specimen.

With this configuration, laser light with a beam diameter that is suitably adjusted by the control apparatus according to the depth of the observation plane is radiated. The inventors of the present application have confirmed experimentally that, as the observation depth increases, the clarity of the observation image of the deep layer portion is improved by stopping down the beam diameter of the radiated laser light to smaller than the original beam diameter of the objective lens for achieving the designed performance. Thus, by varying the radiated beam diameter according to the observation depth, it is possible to acquire an observation image having good resolution at any depth, and it is possible to acquire clear fluorescence images from the surface layer portion to the deep layer portion.

In the multiphoton-excitation observation apparatus described above, the control apparatus may include a memory unit for storing, in association with each other, observation plane depths in the specimen and operating levels of the incidence-adjusting unit; may obtain the operating level corresponding to the depth of the observation plane from the memory unit; and may control the incidence-adjusting unit with the obtained operating level.

Thus, by providing the memory unit for storing the observation plane depths and the optimum operating levels in association with each other, it is possible to quickly control the incidence-adjusting unit with an operating level that corresponds to the observation depth. Accordingly, it is possible to adjust the beam diameter of the laser light to the optimum diameter for the depth of the observation plane.

The information stored in the memory unit is obtained as described below, for example.

For instance, by adjusting the incidence-adjusting unit in a predetermined operating range with at least two reference depths selected in an observation range related to the depth direction of the specimen and with the observation plane set at a reference depth, the beam diameter of the laser light is varied and the operating level of the incidence-adjusting unit that is optimal for each reference depth is specified from the observation image acquired at this time. Then, the optimum operating level for each observation plane depth is determined based on the relationship between the reference depth and the operating level of the incidence-adjusting device and is stored in the memory unit.

In the multiphoton-excitation observation apparatus described above, the control apparatus may adjust the intensity of the laser light irradiating the specimen according to the depth of the observation plane in the specimen.

With this configuration, the pulsed laser light emitted from the light-source unit is supplied to the observation apparatus main unit and irradiates the specimen. In the specimen, multiphoton-absorption occurs at the position where the laser light is focused, generating fluorescence. This fluorescence is detected and observed by the observation apparatus main unit.

In this case, when the depth of the observation plane changes, by operating the control apparatus, the laser light irradiating the specimen (excitation light) is adjusted to an intensity corresponding to the depth of the observation plane. For example, the intensity of the laser light irradiating the specimen is adjusted so as to increase as the depth of the observation plane increases. Accordingly, laser light with an intensity that is suitable for the depth of the observation plane is radiated; therefore, it is possible to effectively generate multiphoton absorption at any depth, which allows clear fluorescence images to be acquired from the surface layer portion to the deep layer portion. The control apparatus adjusts the intensity of the laser light irradiating the specimen by controlling the intensity of the laser light or the oscillation frequency.

Furthermore, according to this invention, it is not necessary to perform image processing afterwards, and therefore, the processing involved can be simplified.

In the multiphoton-excitation observation apparatus described above, the control apparatus may include a memory unit for storing, in association with each other, observation plane depths in the specimen and laser light intensities; may obtain from the memory unit the laser light intensity corresponding to the depth of the observation plane; and may control the light-source unit to output the obtained laser light intensity.

With this configuration, when the depth of the observation plane changes, by obtaining from the memory unit information about the intensity of the laser light that is suitable for the depth of the observation plane, it is possible to quickly and easily adjust the intensity of the laser light to the optimum level. As a result, it is possible to quickly vary the intensity of the laser light irradiating the specimen according to the depth of the observation plane.

The information stored in the memory unit is obtained as described below, for example.

For instance, by varying the intensity of the laser light in a predetermined range and analyzing the observation image acquired at this time, with at least two reference depths selected in an observation range related to the depth direction of the specimen and with the observation plane set at a reference depth, the optimum light intensity for each reference depth is specified. Then, the optimum light intensity for each observation plane depth is determined using the relationship between the reference depth and light intensity and is stored in the memory unit.

In the multiphoton-excitation observation apparatus described above, the control apparatus may include a memory unit for storing, in association with each other, observation plane depths in the specimen and numbers of irradiated pulses of laser light; may obtain from the memory unit the number of irradiated pulses of laser light corresponding to the depth of the observation plane; and may control the light-source unit to output the obtained number of irradiated pulses.

With this configuration, when the depth of the observation plane changes, by obtaining from the memory unit the intensity of the laser light corresponding to the depth of the observation plane, it is possible to adjust the intensity of the laser light quickly and easily. As a result, it is possible to quickly vary the intensity of laser light irradiating the specimen according to the depth of the observation plane.

The information stored in the memory unit is determined as described below, for example.

For instance, with at least two reference depths selected within an observation range related to the depth direction of the specimen and with the observation plane set at a reference depth, the number of radiated pulses of laser light is varied in a predetermined range, and the optimum number of radiated pulses at each reference depth is specified from the observation image acquired at this time. Then, the optimum number of radiated pulses for each observation plane depth is determined based on the relationship between reference depth and light intensity and is stored in the memory unit.

The multiphoton-excitation observation apparatus described above may further comprise an input unit for inputting items to be stored in the memory unit.

With this configuration, it is possible to easily change and set the associated information stored in the memory unit according to the conditions.

The multiphoton-excitation observation apparatus described above may further comprise a laser scanning unit for scanning the laser light emitted from the light-source unit; an objective optical system for focusing the laser light scanned by the laser scanning unit in the specimen; and a light-detecting device for detecting fluorescence emitted from the focal position of the laser light in the specimen. The light-detecting device may include a detector for outputting a detection signal according to the incident fluorescence; and a detector controller for adjusting a detection sensitivity of the fluorescence in the detector according to the depth of the observation plane in the specimen.

With the configuration described above, the laser light emitted from the light-source unit is scanned by the laser scanning unit and focused in the specimen by the objective optical system. Therefore, fluorescence is generated due to multiphoton absorption at the focal position in the specimen. This fluorescence is guided to the light detecting device, and by detecting the fluorescence, the internal state at a predetermined position in the depth direction of the specimen is observed as a fluorescence image. In such a case, when the depth of the observation plane changes, the detection sensitivity of the detector is adjusted by the operation of the detection controller; therefore, it is possible to effectively acquire the fluorescence generated at the observation plane, and it is possible to acquire clear observation images from the surface layer portion to the deep layer portion.

In the multiphoton-excitation observation apparatus described above, the detection controller may adjust at least one of the sensitivity of photo-electric conversion and an integration time of the output signal in the detector.

With this configuration, when the depth of the observation plane changes, the detection controller adjusts at least one of the sensitivity of the photo-electric conversion and the integration time of the output signal in the detector. For example, as the depth of the observation plane increases, at least one of the sensitivity of photoelectric conversion and the integration time is adjusted so as to increase. Accordingly, it is possible to effectively acquire the fluorescence generated in the observation plane, and it is possible to acquire clear fluorescence images from the surface layer portion to the deep layer portion. Furthermore, according to the present invention, it is possible to vary the intensity before the image data is stored in the memory according to the depth of the observation plane. Therefore, compared to a case where image processing is performed afterwards, such as in the technique disclosed in Japanese Unexamined Patent Application, Publication No. 2000-275541, the degree of freedom of adjustment can be increased, and it is possible to save image data in the optimum state.

In the multiphoton-excitation observation apparatus described above, the light-detecting device may include a pin-hole, and the detection controller may adjust an opening diameter of the pin-hole.

With this configuration, when the depth of the observation plane changes, the detection controller adjusts the opening diameter of the pinhole provided in the light detecting device. For example, as the depth of the observation plane increases, the opening diameter of the pinhole is adjusted so as to increase. Accordingly, it is possible to effectively acquire the fluorescence generated by multiphoton absorption in the observation plane, and it is possible to acquire clear fluorescence images from the surface layer portion to the deep layer portion. Also, it is possible to vary the light intensity before the image data is stored in the memory according to the depth of the observation plane. Therefore, compared to a case in which image processing is performed afterwards, such as in the technique disclosed in Japanese Unexamined Patent Application, Publication No. 2000-275541, the degree of freedom of adjustment can be increased, and it is possible to save image data in the optimum state.

The present invention affords an advantage in that it can acquire clear images from the surface layer portion to the deep layer portion, even when observing down to a very deep region (for example, a depth of about 100 μm or more from the surface).

DETAILED DESCRIPTION OF THE INVENTION

A multiphoton-excitation observation apparatus 1 according to a first embodiment of the present invention will be described below with reference to FIGS. 1 to 4.

Figure 1:
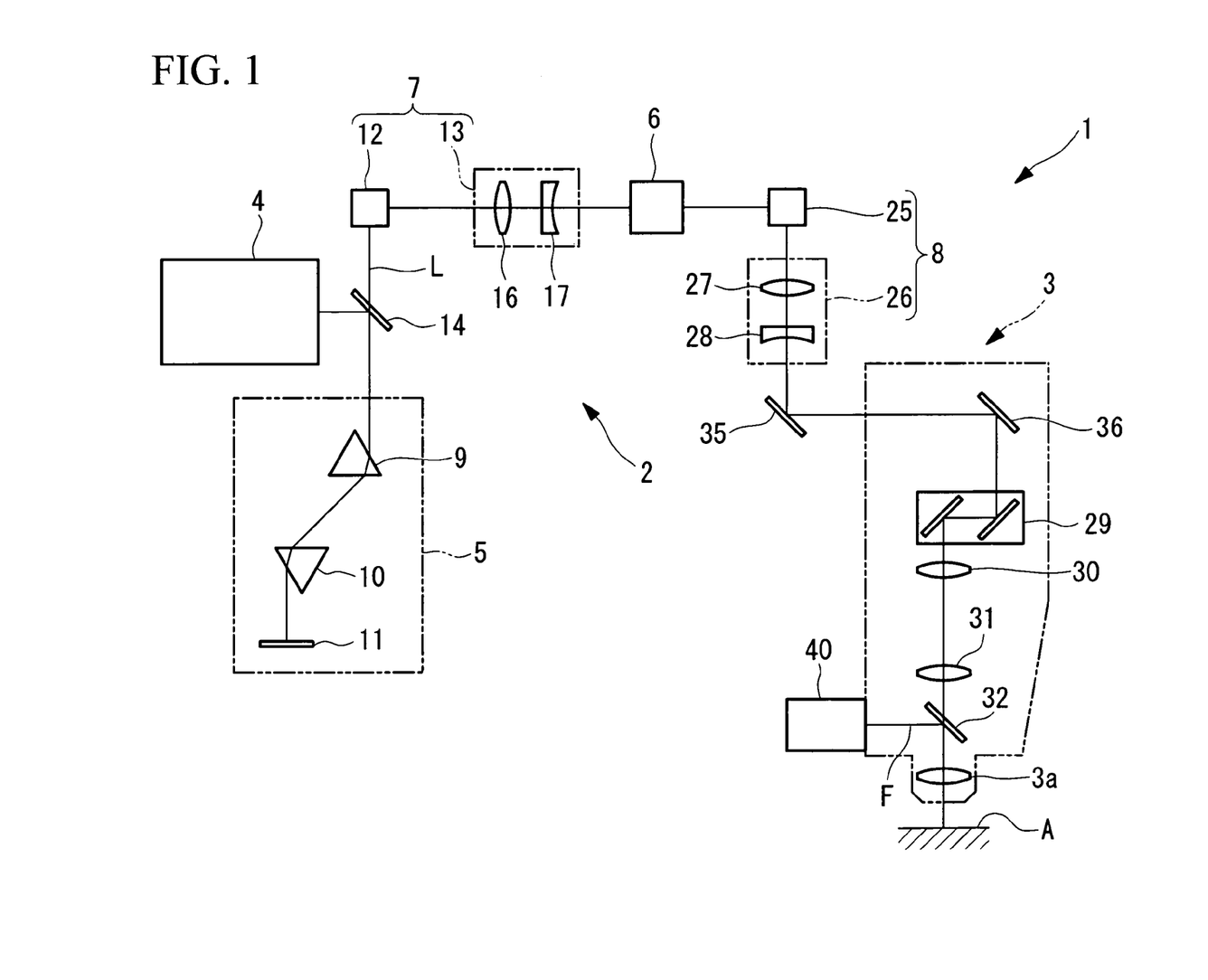
FIG. 1 is a block diagram illustrating, in outline, a multiphoton-excitation observation apparatus according to a first embodiment of the present invention.

As shown in FIG. 1, the multiphoton-excitation observation apparatus 1 according to this embodiment is, for example, a multiphoton-excitation microscope including a light-source unit 2 and a fluorescence microscope main unit (observation apparatus main unit) 3 disposed after the light-source unit 2.

The light-source unit 2 includes a pulsed laser light source 4 for emitting ultra-short pulsed laser light L; a dispersion-compensating optical system 5 for compensating for group velocity dispersion of the ultra-short pulsed laser light L emitted from the pulsed laser light source 4; an acousto-optic device 6 for performing on/off or intensity modulation of the dispersion-compensated ultra-short pulsed laser light L; an incidence-adjusting unit 7, disposed between the acousto-optic device 6 and the pulsed laser light source 4, for aligning the ultra-short pulsed laser light L incident on the acousto-optic device 6; and a microscope incidence-adjusting unit 8 for adjusting the ultra-short pulsed laser light L emitted from the acousto-optic device 6 and entering the fluorescence microscope main unit 3.

The dispersion-compensating optical system 5 is formed, for example, of a pair of prisms 9 and 10 and a mirror 11. Alternatively, it may be formed of a pair of gratings. Adjusting the gap between the prisms 9 and 10, or the gap between the gratings, adjusts the optical path length of each wavelength, thus compensating for the group velocity dispersion in the entire optical system from the pulsed laser light source 4 to an objective lens 3a in the fluorescence microscope main unit 3.

The incidence-adjusting unit 7 includes an alignment adjusting device 12 and a beam-shaping optical system 13.

The alignment adjusting device 12 includes, for example, two mirrors whose position and angle can be adjusted and is configured so as to adjust the position and deflection of the optical axis of the ultra-short pulsed laser light L to make it incident on the acousto-optic device 6 with a suitable position and angle with good precision. Reference numeral 14 in the figure is a mirror which, at one side, reflects the ultra-short pulsed laser light L emitted from the pulsed laser light source 4 towards the dispersion-compensating optical system 5 and which is disposed at a position away from, in a direction orthogonal to the plane of the drawing, the optical axis of the ultra-short pulsed laser light L output from the dispersion-compensating optical system 5.

The beam-shaping optical system 13 is configured to stop down the beam diameter of the ultra-short pulsed laser light L passing through the dispersion-compensating optical system 5 and positioned by the alignment adjusting device 12 so as to fall inside an effective area X of a crystal 15 (see FIG. 2) in the acousto-optic device 6.

In this embodiment, the beam-shaping optical system 13 is formed, for example, of a Galilean beam expander combining a biconvex lens 16 and a plano-concave lens 17. The beam-shaping optical system 13 is preferably disposed between the pulsed laser light source 4 and the acousto-optic device 6, closer to the acousto-optic device 6 from the center thereof. The beam-shaping optical system 13 is preferably disposed at a location 100 to 1000 mm in front of the acousto-optic device 6.

Figure 2:
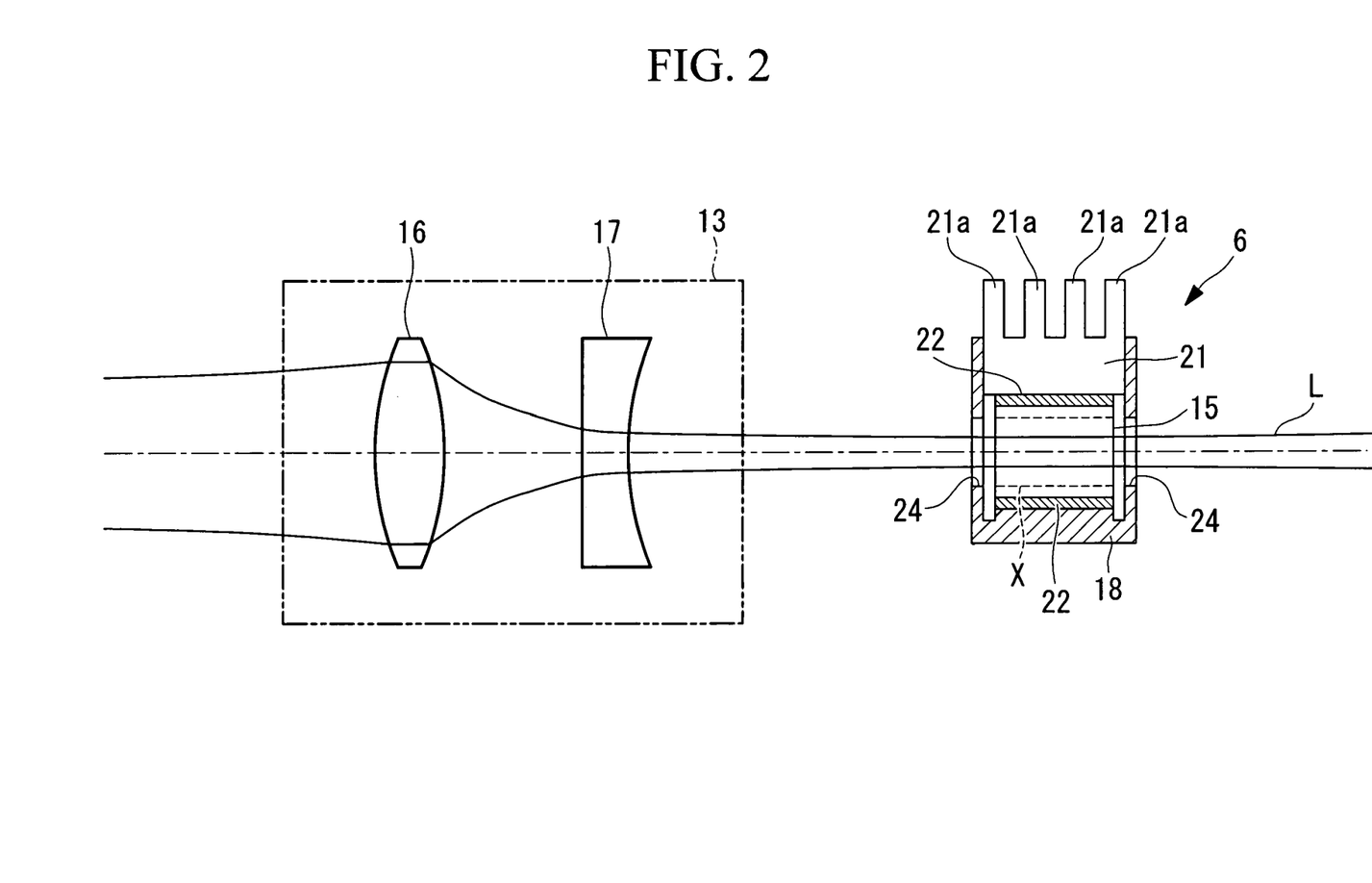
FIG. 2 is a perspective view showing an example of an acousto-optic device used in the multiphoton-excitation observation apparatus in FIG. 1.

As shown in FIG. 2, the acousto-optic device 6, which is an AOM for example, includes the crystal 15 formed of tellurium dioxide, a case 18 for holding the crystal 15, a transducer (not shown in the drawing) formed of a piezoelectric element bonded to the crystal 15, an acoustic-wave-generating electrical circuit (not shown in the drawing) for transmitting an electrical signal to be input to the transducer, and a heat sink (heat-dissipating member) 21 bonded to the crystal 15. An interfacing member 22 formed, for example, of indium foil or a thermal compound, such as silicone grease, is provided between the crystal 15 and the case 18 and between the crystal 15 and the heat sink 21.

Openings 24 are provided in the opposing side walls of the case 18 on either side of the crystal 15; the ultra-short pulsed laser light L is introduced from one of the openings 24, and after passing through the crystal 15, the ultrashort-pulsed laser light L is emitted from the other opening 24.

The heat sink 21 is formed, for example, of a material having high thermal conductivity, such as aluminum or an aluminum alloy, and includes a plurality of flat plate-shaped fins 21a arranged in parallel with gaps therebetween.

The microscope incidence-adjusting unit 8 includes an alignment adjusting device 25 and a collimating optical system 26.

The alignment adjusting device 25 has the same construction as the alignment adjusting device 12 and can adjust the position and deflection of the optical axis of the ultra-short pulsed laser light L entering the fluorescence microscope main unit 3 with good precision.

The collimating optical system 26 is formed, for example, of a Galilean beam expander of the same type as the beam-shaping optical system 13, including a biconvex lens 27 and a plano-concave lens 28. The collimating optical system 26 adjusts the beam diameter and the beam divergence of the emitted ultra-short pulsed laser light L so that the ultra-short pulsed laser light L whose beam diameter and beam divergence are controlled by the beam-shaping optical system 13 so as to completely pass through the effective area X of the acousto-optic device 6 and whose optical axis position and deflection are adjusted by the alignment adjusting device 25 forms a beam waist at a predetermined position (predetermined position in a specimen A) in front of the objective lens 3a of the fluorescence microscope main unit 3. More concretely, the collimating optical system 26 adjusts the beam diameter and the beam divergence thereof so that, at the pupil position of the objective lens 3a, the ultra-short pulsed laser light L has substantially the same beam diameter as that pupil diameter.

The fluorescence microscope main unit 3 includes a two-dimensional scanning mechanism 29 for two dimensionally scanning the ultra-short pulsed laser light L; a pupil projection lens 30 for condensing the two-dimensionally scanned ultra-short pulsed laser light L to form an intermediate image; an image-forming lens 31 for collecting and substantially collimating the ultra-short pulsed laser light L forming the intermediate image; the objective lens 3a for focusing the substantially collimated ultra-short pulsed laser light L and imaging it at the specimen A; a dichroic mirror 32 for splitting off from the ultra-short pulsed laser light L fluorescence F emitted due to multiphoton absorption in the specimen A and collected by the objective lens 3a; and a light detecting device 40 for detecting the fluorescence F that is split off. Reference numerals 35 and 36 are mirrors. The two-dimensional scanning mechanism 29 is formed of two galvanometer mirrors (not shown in the drawing) that can be rocked back and forth about two mutually orthogonal axes and that are disposed in close proximity to each other, that is, so-called proximity galvanometer mirrors.

Figure 3:
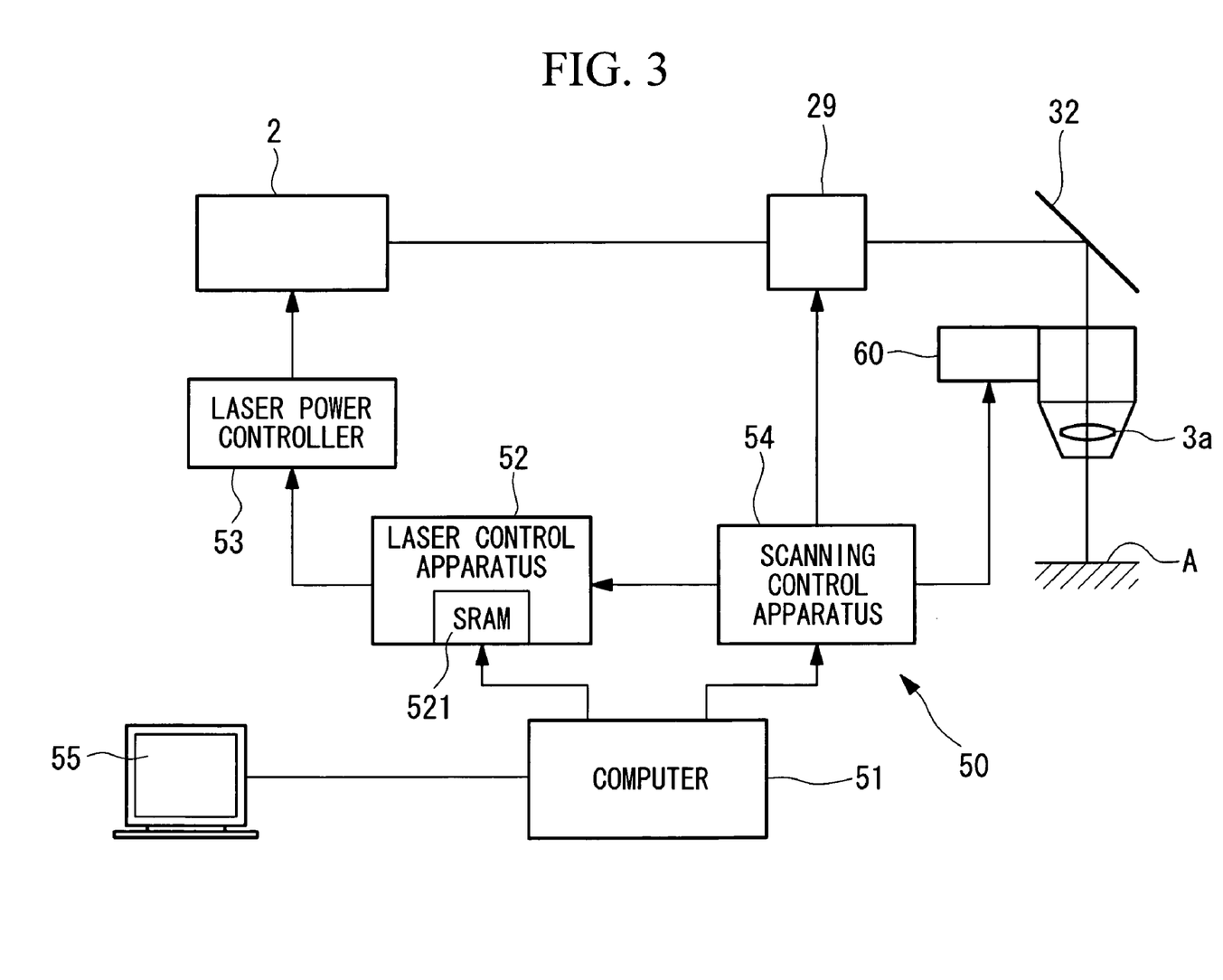
FIG. 3 is a diagram showing an example of a control system in the multiphoton-excitation observation apparatus shown in FIG. 1.

FIG. 3 illustrates, in outline, the configuration of a control system for controlling the individual components of the multiphoton-excitation observation apparatus 1 shown in FIG. 1. In FIG. 3, parts identical to those in FIG. 1 described above are assigned the same reference numerals, and a description thereof is omitted.

As shown in FIG. 3, a control apparatus 50 provided in the multiphoton-excitation observation apparatus 1 includes a computer 51, a laser control unit 52, a laser power controller 53, and a scanning control unit 54.

The computer 51, which has an internal user interface such as a GUI, causes laser light (excitation light) to irradiate a predetermined observation plane in the specimen by outputting control commands to the laser control unit 52 and the scanning control unit 54 based on an observation schedule defined by the user. In addition, by acquiring digital data from the light detecting device 40 shown in FIG. 1, converting this data to an image, and outputting it on a monitor 55, the computer 51 supplies the user with an observation image of the predetermined observation plane in the specimen A.

The laser control unit 52 includes an internal SRAM (memory unit) 521. A lookup table in which observation plane depths in the specimen A and optimum laser intensities are associated is recorded in this SRAM-521. The laser control unit 52 acquires the optimum laser intensity for the depth of the observation plane by referring to the lookup table in the SRAM 521 based on a synchronization signal from the scanning control unit 54, which will be described later, and outputs an intensity command according to this laser intensity to the laser power controller 53. By controlling the acousto-optic device 6 or the laser light source 4 itself, which are provided in the light-source unit 2, based on the intensity command from the laser control unit 52, the laser power controller 53 adjusts the intensity of the laser beam introduced to the fluorescence microscope main unit 3.

Accordingly, pulsed light with the optimum intensity for the depth of the observation plane in the specimen A is emitted from the light-source unit 2.

On the other hand, the scanning control unit 54 scans the pulsed laser light emitted from the light-source unit 2 in the X and Y directions on the observation plane in the specimen A by scanning the two-dimensional scanning mechanism 29 based on a control command from the computer 51. In addition, by adjusting the distance between the objective lens 3a and the specimen A by driving a Z-axis driving mechanism 60 to focus the laser light at the predetermined observation plane in the specimen A, it produces a multiphoton-excitation effect at that position.

The scanning control unit 54 outputs to the laser control unit 52 a synchronization signal with a timing for driving the Z-axis driving mechanism 60. Accordingly, the laser control unit 52 can keep track of variations in the depth of the observation plane in the specimen A.

When observing the specimen with the multiphoton-excitation observation apparatus 1 having the above-described configuration, a prescan is performed first to serve as a reference.

In the prescan, images are acquired when the observation plane is respectively set at the top (hereinafter referred to as "surface layer portion") and at the bottom (hereinafter referred to as "deep layer portion") in the Z-direction (depth) of the observation, input by the user. More specifically, by driving the Z-axis driving mechanism 60, the observation plane in the specimen A is set at the deep layer portion, and light is radiated in this state. At this time, the laser power controller 53 gradually increased the intensity of the laser light from its minimum value based on a command from the laser control unit 52. The user checks the observation image displayed on the monitor 55 and records in the computer 51 the laser intensity at which the clearest image is obtained.

Next, the observation plane in the specimen A is set at the surface layer portion by driving the Z-axis driving mechanism 60, and laser light is radiated in this state. At this time, substantially the same as described above, the laser power controller 53 gradually increased the laser intensity from the minimum value based on a command from the laser control unit 52. The user checks the observation image displayed on the monitor 55 and records in the computer 51 the light intensity at which an image having the same brightness as that previously confirmed at the deep layer portion is obtained.

Figure 4:
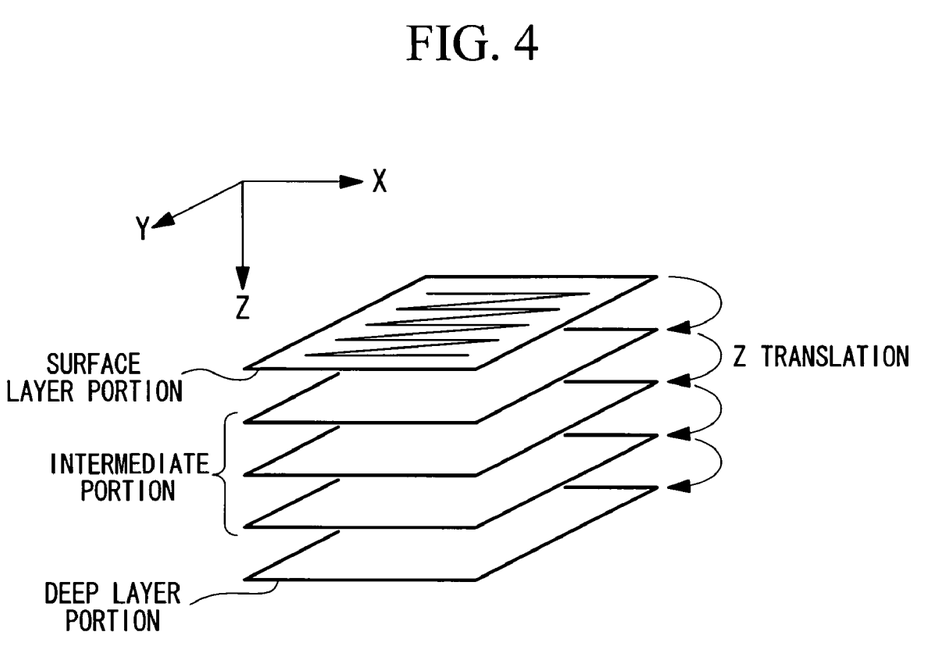
FIG. 4 is a diagram for explaining observation planes in a surface layer portion, an intermediate portion, and a deep layer portion.

Then, the light intensity at the intermediate portion (in layers between the deep layer portion and the surface layer portion) is obtained by using the light intensity at the deep layer portion and the light intensity at the surface layer portion (see FIG. 4).

In general, because the light intensity is reduced due to scattering in the medium inside the specimen as the depth of the observation plane increases, it is possible to obtain the light intensity at the intermediate portion from the dispersion relation inside the medium, shown in Equation (1) below:

$$\nabla[D(r)\nabla\Phi(r)]-\mu_a(r)\Phi(r)+q=0 \quad (1)$$

$\Phi(r)$, $D(r)=1/3\ \mu_s(r)$, $\mu_s(r)$, $\mu_a(r)$, and q are the integrated intensity of the light, the optical diffusion coefficient, the equivalent dispersion coefficient, the absorption coefficient, and the light source intensity (=0) inside the medium, at respective positions r.

Instead of using the relation shown in (1) above, the optimum light intensity in the intermediate portion may be determined using a standard interpolation method, for example, linear interpolation or polynomial approximation.

Moreover, rather than determining it by calculation, the optimum light intensity corresponding to each observation plane may be determined by performing a prescan for specifying the light intensity, as describe above, for all observation plane depths to be observed.

Once the light intensity corresponding to each observation plane is determined by such a procedure, a lookup table associating these pieces of information is created and stored in the SRAM 521 in the laser control unit 52. Accordingly, the intensity of the laser light in the main observation (described later) is adjusted to the light intensity stored in this lookup table.

In the main observation, first, the driving mechanism 60 is driven by the scanning control unit 54, and the observation plane is adjusted to the surface layer portion of the specimen A, whereupon a synchronization signal is output from the scanning control unit 54 to the laser control unit 52. Upon receiving this synchronization signal, the laser control unit 52 obtains the laser intensity corresponding to the surface layer portion from the lookup table recorded in the SRAM 521 and outputs an intensity command corresponding to this laser intensity to the laser power controller 53. Accordingly, by controlling the light-source unit 2 with the laser power controller 53 based on this intensity command, pulsed laser light having the optimum intensity for the observation plane is emitted from the light-source unit 2. The ultra-short pulsed laser light L emitted from the light-source unit 2 is emitted towards the microscope main unit 3 shown in FIG. 1.

The ultra-short pulsed laser light L incident on the microscope main unit 3 is two-dimensionally scanned by the two-dimensional scanning mechanism 29, which is scanned by the scanning control unit 54, and then passes through the pupil-projection lens 30, the image-forming lens 31, the dichroic mirror 32, and the objective lens 3a, is focused onto the surface layer of the specimen A, is two-dimensionally scanned in the X and Y directions on this surface layer, producing a multiphoton excitation effect. Fluorescence F generated by this multiphoton-excitation effect is split off by the dichroic mirror 32 and is guided to the light detecting device 40. The light detecting device 40 detects the intensity of this light and outputs digital data corresponding to the detected intensity to the computer 51 shown in FIG. 2. Accordingly, an observation image of the surface layer is produced by the computer 51 and is then displayed on the monitor 55.

Subsequently, when the scanning control unit 54 finishes scanning the laser beam in the X and Y directions, by adjusting the Z-axis driving mechanism 60, the observation plane in the specimen A is positioned at the next depth, for example, at the shallowest depth in the intermediate portion (see FIG. 4), and in addition, a synchronization signal is output to the laser control unit 52. When the laser control unit 52 receives the synchronization signal, it obtains the laser intensity corresponding to the depth of the observation plane from the lookup table recorded in the SRAM 521 and outputs it to the laser power controller 53. Accordingly, observation is carried out at the optimal light intensity for the next observation plane depth.

Thus, each time the depth of the observation plane changes in this way, pulsed laser light with an intensity corresponding to that depth is focused onto the observation plane in the specimen A, and as shown in FIG. 4, respective observation images for each depth are acquired.

As described above, according to the multiphoton-excitation observation apparatus 1 of this embodiment, when the depth of the observation plane changes, the pulsed laser light is adjusted to the optimum intensity for the depth of the observation plane and is focused on the observation plane in the specimen A. Therefore, it is possible to effectively generate multiphoton excitation at the observation plane, which allows clear fluorescence images to be acquired from the surface layer portion to the deep layer portion.

When the depth of the observation plane changes, it is possible to easily obtain the optimum laser light intensity for the depth of the observation plane by referring to the lookup table recorded in the SRAM 521, and therefore, it is possible to rapidly adjust the intensity of the laser light. As a result, it is possible to rapidly vary the intensity of the pulsed laser light irradiating the specimen according to the depth of the observation plane.

Furthermore, regarding the ultra-short pulsed laser light L, since the optical axis position and angle are adjusted by the alignment adjusting optical system 5 and the beam diameter and beam divergence thereof are adjusted by the beam-shaping optical system 7, it can be focused onto each observation plane in the specimen A with high precision. Therefore, it is possible to acquire fluorescence images with high spatial resolution.

In the multiphoton-excitation observation apparatus 1 according to this embodiment, the intensity (peak power) of the laser light is adjusted according to the depth of the observation plane; instead of this, however, it is possible to change the number of pulses of laser light irradiating the specimen. Changing the number of pulses irradiating the specimen can be achieved by changing the pulse oscillation frequency in the pulsed laser light source 4 or temporally blocking some of the laser pulses (pulse thinning) using high-speed shuttering means, such as the acousto-optic device 6. Since it is possible to vary the intensity of the laser light irradiating the observation plane in the specimen in this way, it is possible to achieve the same effect as when varying the intensity of the laser light as described above.

Next, a multiphoton-excitation observation apparatus 100 according to a second embodiment of the present invention will be described below with reference to FIG. 5.

The multiphoton-excitation observation apparatus 100 according to this embodiment changes the beam diameter of the laser light according to the depth of the observation plane in the specimen.

In the description of this embodiment, parts having the same configuration as those in the above-described multiphoton-excitation observation apparatus 1 according to the first embodiment are assigned the same reference numerals, and a description thereof is omitted here.

Figure 5:
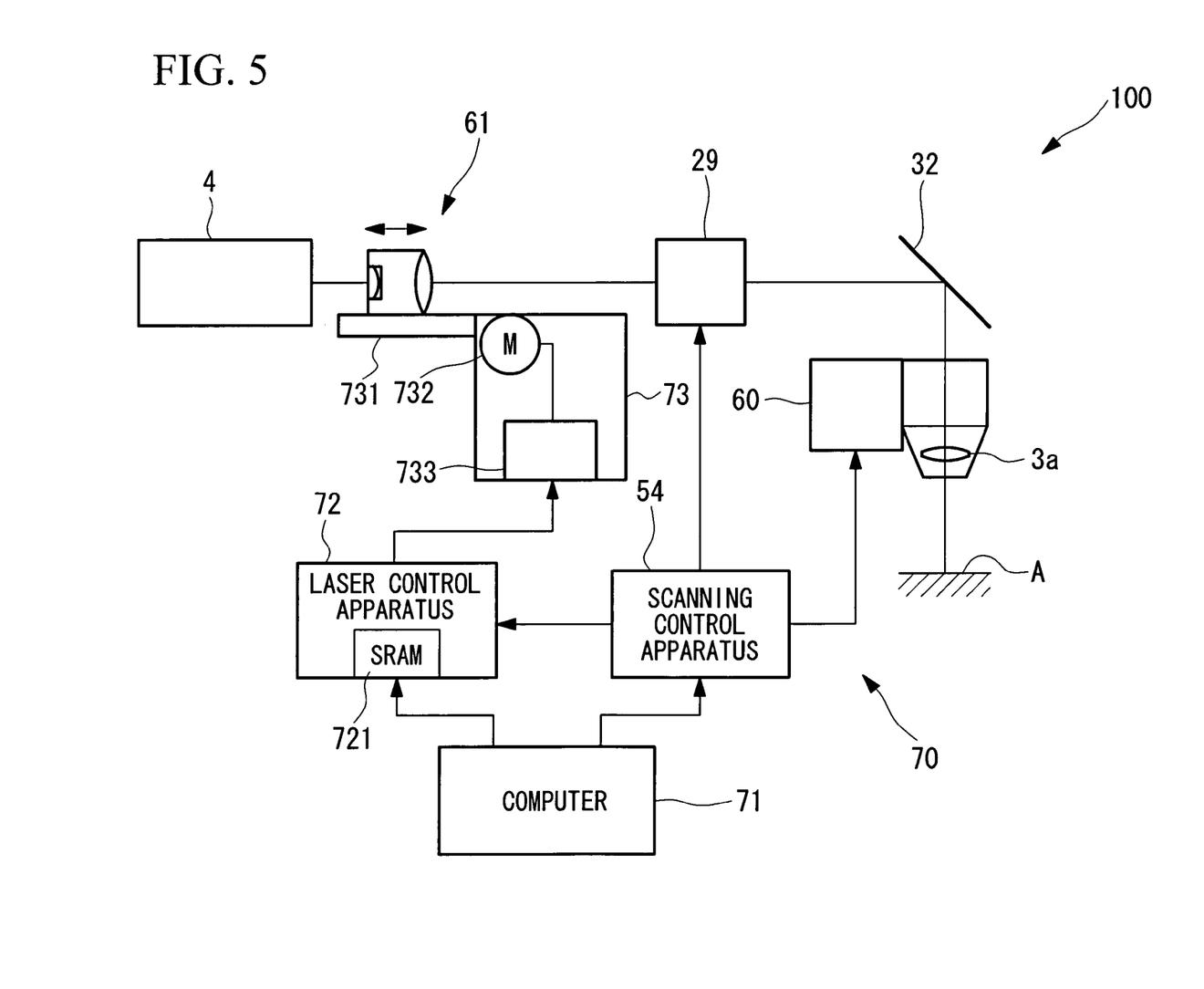
FIG. 5 is a diagram showing an example of the control system in a multiphoton-excitation observation apparatus according to a second embodiment of the present invention.

FIG. 5 shows, in outline, the principal components of the multiphoton-excitation observation apparatus 100 according to this embodiment.

As shown in FIG. 5, the multiphoton-excitation observation apparatus 100 according to this embodiment includes, between the pulsed laser light source 4 and the fluorescence microscope main unit 3, an incidence-adjusting unit for varying the beam diameter of the pulsed laser light emitted from the pulsed laser light source 4. As this incidence-adjusting unit, it is possible to employ, for example, a collimator lens optical system 61 which collimates the light emitted from the pulsed laser light source 4. When employing the collimator lens optical system 61 as the incidence-adjusting unit, by changing the position of the collimator lens optical system 61 relative to the optical-axis direction of the pulsed laser light, the collimating relationship is changed, which allows the beam diameter at the pupil position of the objective lens 3$a$ to be changed. Accordingly, it is possible to change the beam diameter of the laser light focused at the observation plane in the specimen A.

A control apparatus 70 of the multiphoton-excitation observation apparatus 100 includes, instead of the laser power controller 53 shown in FIG. 3, a motorized driving unit 73 which can move the collimator lens optical system 61 in the optical-axis direction and includes, instead of the laser control unit 52, a laser control unit 72.

The motorized driving unit 73 includes a linear rail 731 which can move the collimator lens optical system 61 in the optical-axis direction, a stepping motor 732 having a rack and pinion gear, and a motor driver 733 for driving the stepping motor 732.

The laser control unit 72 includes an internal SRAM (memory unit) 721. A lookup table in which observation plane depths in the specimen A and optimal positions of the collimator optical system 61 are associated with each other is stored in the SRAM 721.

By referring to the lookup table in the SRAM 721 based on a synchronization signal from the scanning control unit 54, the laser control unit 72 obtains the optimal position of the collimator lens optical system 61 for the depth of the observation plane and outputs to the motorized driving unit 73 a control command for moving the collimator lens optical system 61 to this position. The motorized driving unit 73 controls the stepping motor 732 on the basis of the control command from the laser control unit 72. Accordingly, the collimator lens optical system 61 is moved on the linear rail by a distance corresponding to the control level of the stepping motor 732 and stops at the lens position corresponding to the depth of the observation plane.

Thus, pulsed laser light with the optimum beam diameter for the depth of the observation plane in the specimen A is output from the light-source unit 2.

The creation of the lookup table described above is carried out by the following procedure, which is similar to that used in the first embodiment described above.

First, the observation plane in the specimen is set in the deep layer portion, and laser light is radiated in this state. By gradually changing the position of the collimator lens optical system 6 during this time, the beam diameter of the pulsed laser light is gradually stopped down. The user checks the observation image displayed on the monitor 55 and records in the computer 51 the position of the collimator lens optical system 61 at which the clearest image is acquired.

Then, the observation plane in the specimen A is set at the surface layer portion by driving the driving mechanism 60, and laser light is radiated in this state. By moving the position of the collimator lens optical system 61 in a similar fashion, the beam diameter of the pulsed laser light is stopped down. The user checks the observation image displayed on the monitor 55 and records in the computer 51 the position of the collimator lens optical system 61 at which the clearest image is acquired. Setting the surface layer portion at the surface of the specimen automatically sets a beam diameter realizing the original performance of the objective lens 3$a$; in this case, therefore, it is not necessary to record the position in a prescan, as described above.

When the light intensity at the deep layer portion and the light intensity at the surface layer portion are specified in this way, the position of the collimator lens optical system 61 in the intermediate portion (in layers between the deep layer portion and the surface layer portion) is determined using these values. The position setting in the intermediate portion is the same as that used in the first embodiment described above, that is, based on the optical dispersion relation of the medium, shown in Equation (1). In addition to using a standard interpolation method, the optimum lens position for each depth can be determined by performing prescans for all depths of the observation planes to be observed.

When the lens position for each observation plane is determined using this procedure, the computer 71 creates a lookup table in which these pieces of information are associated and stores it in the SRAM 721 in the laser control unit 72. Accordingly, in the main observation, laser light with the optimum beam diameter is focused at the observation plane by adjusting the position of the collimator lens optical system 61 according to the depth of the observation plane.

Details of the control carried out by the control apparatus 70 in the main observation are the same as in the first embodiment described above, and therefore, a description thereof is omitted here.

As described above, with the multiphoton-excitation observation apparatus 100 according to this embodiment, because the beam diameter of the laser light is changed according to the depth of the observation plane in the specimen, it is possible to solve the problem related to nonuniformity of the refractive index, which depends on the depth of the observation plane in the specimen. Accordingly, it is possible to acquire clear fluorescence images from the surface layer portion to the deep layer portion.

For example, when examining the interior (deep part) of a specimen having a different refractive index from the refractive index of a design immersion medium of the objective lens (a medium assumed to fill the space between the tip of the lens and the focal plane in the design of the objective lens), since observation is performed under different conditions from the design conditions of the objective lens, the diameter of the focal spot of laser light focused by the objective lens becomes larger than under ideal conditions. When the laser spot diameter increases, the resolution decreases, and the multiphoton absorption coefficient during multiphoton-excitation observation is reduced, which leads to a reduction in fluorescence intensity. With this embodiment, in contrast, since the beam diameter is adjusted so as to be reduced according to the Z depth being observed, it is possible to suppress an increase in the spot diameter due to the nonuniformity of the refractive index, as described above.

In this embodiment, the collimator lens optical system 61 is used as the incidence-adjusting unit for adjusting the beam diameter of the pulsed laser light emitted from the pulsed laser light source 4. However, the incidence-adjusting unit is not limited to this example, and another optical system may be used.

Furthermore, instead of shifting the position of the entire collimator lens optical system 61, a system including a motorized zoom optical system (for example, a focal zoom lens or the like) that changes the beam diameter without affecting the collimation conditions may be used. The motorized driving unit 73 is not limited to the configuration described above; it is possible to use an actuator that is capable of high-precision positioning, for example, a piezo actuator.

In this embodiment, the position of the lens is set according to the depth of the observation plane in the lookup table. However, it is not limited to this example; it is also possible to store the number of differential pulses of the stepping motor, and so forth. In other words, any type of information can be used instead of the lens position, so long as it allows the position of the lens to be set.

Next, a multiphoton-excitation observation apparatus according to a third embodiment of the present invention will be described below with reference to FIG. 6.

The multiphoton-excitation observation apparatus according to this embodiment performs effective light detection to acquire clear observation images by adjusting the control of each component provided in the light-detecting device 40 according to the depth of the observation plane in the specimen A.

Parts having the same configuration as those in the multiphoton-excitation observation apparatus 1 according to the first embodiment described above are assigned the same reference numerals, and a description thereof is omitted in the description of this embodiment.

Figure 6:
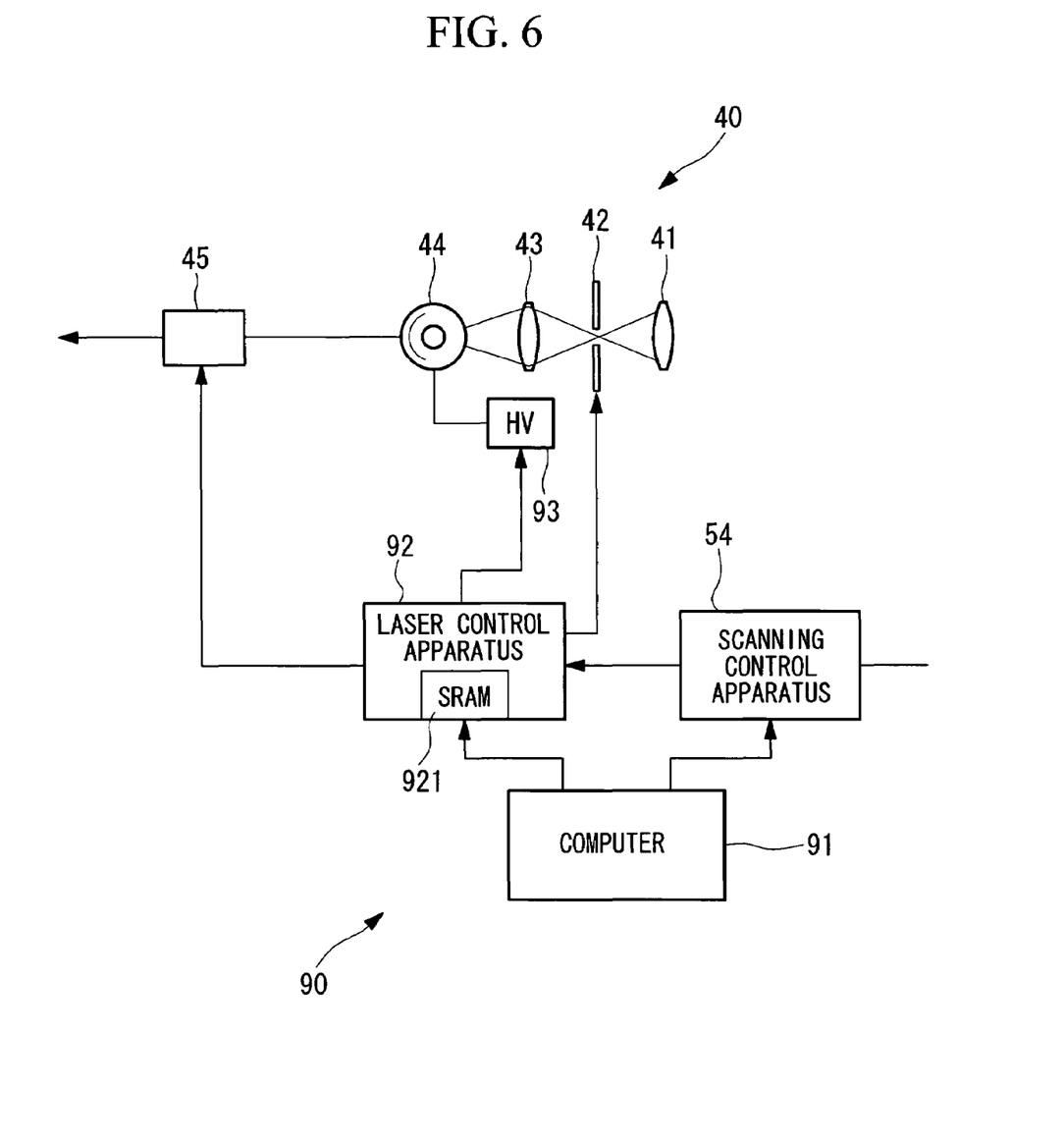
FIG. 6 is a diagram showing an example of the control system in a multiphoton-excitation observation apparatus according to a third embodiment of the present invention.

As shown in FIG. 6, the light-detecting device 40 according to this embodiment includes a focusing lens 41 for focusing fluorescence split off by the dichroic mirror 34 shown in FIG. 1, a pin-hole 42, a lens 43, a photomultiplier tube (PMT; light amplifying unit) 44, and an integrator (integrating unit) 45 for integrating the signal from the photomultiplier tube 44.

The pin-hole 42 may be omitted from the multiphoton-excitation observation apparatus, but providing the pin-hole 42 allows the light detection precision to be improved. The photomultiplier tube 44 detects the fluorescence F passing through the pin-hole 42. The integrator 45 integrates the detection signal output from the photomultiplier tube 44 in a predetermined duration and outputs the integrated signal to a computer 91. The computer 91 generates an observation image from the received signal.

The control apparatus 90 according to this embodiment includes a high-voltage converter 93 instead of the laser power controller 53 shown in the first embodiment and includes a photoreceiver-circuit control apparatus 92 instead of the laser control unit 52. The computer 91 has substantially the same functions as the computer 51 according to the first embodiment described above, but differs in that it outputs a control signal to the photoreceiver-circuit control apparatus 92 instead of to the laser control unit 52.

The high-voltage converter 93 varies the gain of the photomultiplier tube 43 based on a control command from the photoreceiver-circuit control apparatus 92.

The photoreceiver-circuit control apparatus 92 includes an internal SRAM (memory unit) 921. A lookup table in which observation plane depths in the specimen A are associated with pin-hole diameters, gains of the photomultiplier tube 44, and integration times of the integrator 45 is stored in the SRAM 921. By varying the gain and integration time in such a light detecting device 40, it is possible to adjust the detection sensitivity of the light detection, and by varying the pin-hole diameter, it is possible to adjust the detected light intensity.

The photoreceiver control apparatus 92 obtains the optimum control levels for the depth of the observation plane, namely the diameter of the pin-hole 42, the gain of the photomultiplier tube 44, and the integration time of the integrator 45 by referring to the lookup table in the SRAM 921 on the basis of a synchronization signal from the scanning control unit 54, and controls each component based on these control levels. More concretely, as well as adjusting the diameter of the pin-hole 42 to the value obtained from the lookup table, it outputs to the high-voltage converter 93 a control signal for setting the photomultiplier tube 44 to a gain obtained from the lookup table and outputs the integration time to the integrator 45. Accordingly, of the fluorescence incident on the pin-hole 42, a suitable amount of fluorescence F is guided to the photomultiplier tube 44 via the lens 42 and is detected with a gain corresponding to the depth. Then, the detected signal is integrated with the optimum integration time for the depth by the integrator and is output to the computer 91.

To generate the lookup table, similarly to the first embodiment described above, control levels which allow the optimum observation image to be acquired are obtained by varying the control levels of the pin-hole, the photomultiplier tube, and the integrator with the observation plane in the specimen sequentially set at the deep layer portion and the surface layer portion during a prescan. Then, control levels for the intermediate portion are determined from the control levels in the deep layer portion, and the control levels in the surface layer portion and the lookup table is generated by the computer 91 on the basis of these control levels and is written in the SRAM 921 in the photoreceiver-circuit control apparatus 92.

The details of the control performed by the control apparatus 90 in the main observation are the same as in the first embodiment described above, and a description thereof is thus omitted here.

As described above, with the multiphoton-excitation observation apparatus according to this embodiment, when the depth of the observation plane in the specimen A changes, by operating the photoreceiver-circuit control apparatus 92, the diameter of the pin-hole 42, the gain of the photomultiplier tube 44, and the integration time of the integrator 45 in the light detecting device 40 are adjusted according to the depth of the observation plane. For example, as the depth of the observation plane increases, the pin-hole diameter, the gain of the photomultiplier tube, and the integration time of the integrator are adjusted so as to increase. Accordingly, it is possible to effectively acquire a multiphoton-excitation effect generated at the observation plane, and clear fluorescence images can thus be acquired from the surface layer portion to the deep layer portion.

Furthermore, with the multiphoton-excitation observation apparatus according to this embodiment, it is possible to change the light level before the image data is stored in a memory (not shown in the drawing) according to the depth of the observation plane; therefore, for example, compared to a case in which image processing is performed afterwards, the degree of freedom of adjustment can be increased, and image data can be saved under optimum conditions.

In this embodiment, it has been described that the diameter of the pin-hole 42, the gain of the photomultiplier tube 44, and the integration time of the integrator 45 are all adjusted according to the depth of the observation plane. However, it is not limited to this example; any one of these control levels may be adjusted.

Figure 7:
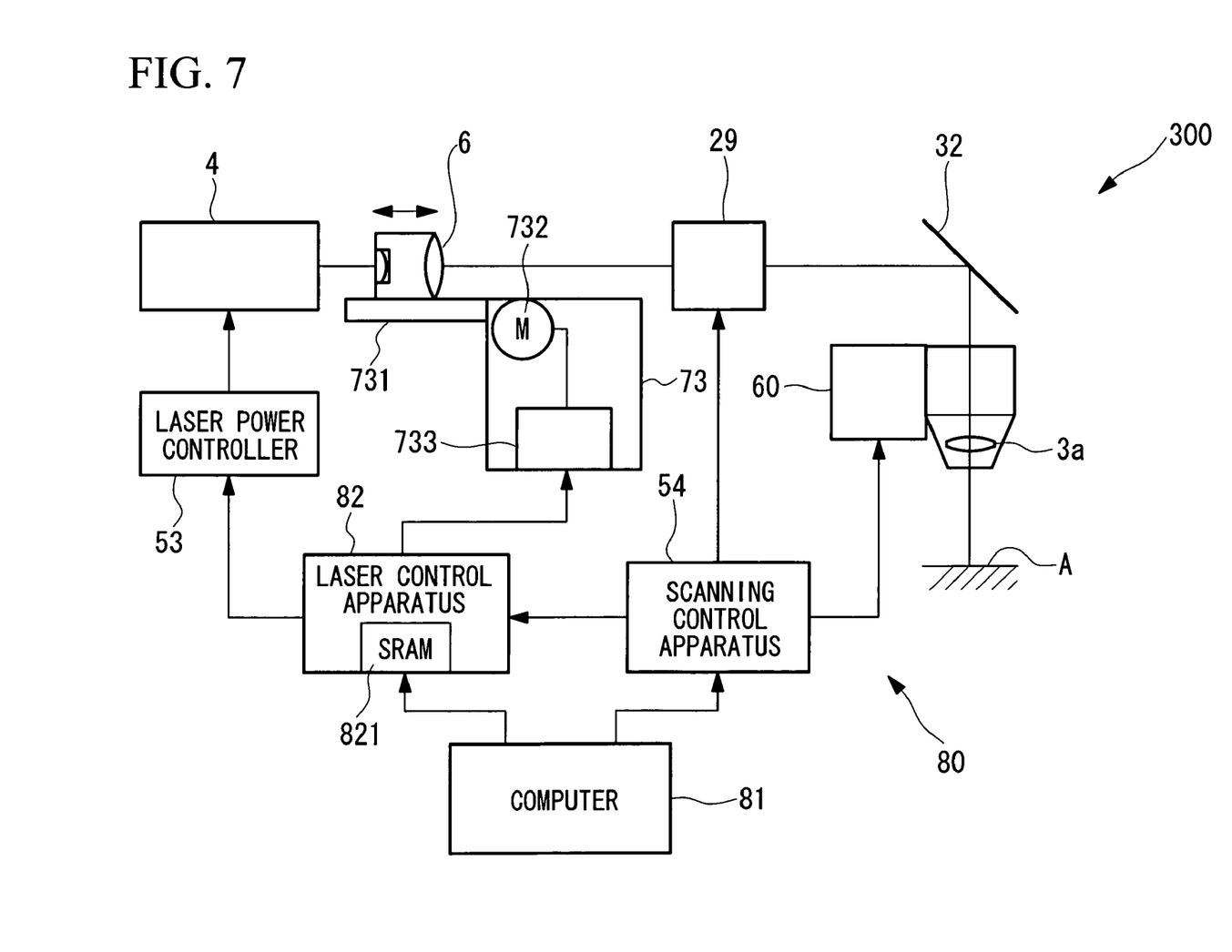
FIG. 7 is a diagram showing an example of the control system in a multiphoton-excitation observation apparatus according to a fourth embodiment of the present invention.

Next, a multiphoton-excitation observation apparatus 300 according to a fourth embodiment of the present invention will be described below with reference to FIG. 7.

The multiphoton-excitation observation apparatus 300 according to this embodiment combines functions of the control apparatus 50 according to the first embodiment (see FIG. 3) and the control apparatus 70 according to the second embodiment (see FIG. 5).

In the description of this embodiment, parts having the same configuration as those in multiphoton-excitation observation apparatuses 1 and 100 according to the first and second embodiments described above are assigned the same reference numerals, and a description thereof is omitted here.

A control apparatus 80 according to this embodiment has a function for varying the intensity of the pulsed laser light according to the depth of the observation plane in the specimen A and a function for varying the beam diameter of the laser light by adjusting the position of the collimator lens optical system 61 according to the depth of the observation plane in the specimen A.

Therefore, a lookup table in which observation plane depths in the specimen A are associated with light intensities and a lookup table in which observation plane depths are associated with beam diameters are stored in an SRAM 821 provided in a laser control unit 82. Thus, by referring to these lookup tables, the intensity and beam diameter of the laser light are adjusted according to the depth of the observation plane. Accordingly, even if the depth of the observation plane changes, it is possible to always acquire clear observation images.

The function implemented by the control apparatus 90 of the multiphoton-excitation observation apparatus according to the third embodiment described above may be added to this multiphoton-excitation observation apparatus 300. Also, a multiphoton-excitation observation apparatus combining functions provided in the control apparatus 70 according to the second embodiment and the control apparatus 90 according to the third embodiment may also be used.

What is claimed is:

1. A multiphoton-excitation observation apparatus comprising:
   a light-source unit;
   an observation apparatus main unit for irradiating a specimen with laser light emitted from the light-source unit and observing fluorescence emitted from the specimen; and
   a control apparatus,
   wherein the light-source unit includes
      a pulsed laser light source for emitting pulsed laser light; and
      an incidence-adjusting unit for adjusting the beam diameter of the laser light emitted from the pulsed laser light source, and
   wherein the control apparatus controls the incidence-adjusting unit according to the depth of an observation plane in the specimen.

2. A multiphoton-excitation observation apparatus according to claim 1, wherein the control apparatus includes a memory unit for storing, in association with each other, observation plane depths in the specimen and operating levels of the incidence-adjusting unit; obtains an operating level corresponding to the depth of the observation plane from the memory unit; and controls the incidence-adjusting unit with the obtained operating level.

3. A multiphoton-excitation observation apparatus according to claim 1, wherein the control apparatus adjusts the intensity of the laser light irradiating the specimen according to the depth of the observation plane in the specimen.

4. A multiphoton-excitation observation apparatus according to claim 3, wherein the control apparatus includes a memory unit for storing, in association with each other, observation plane depths in the specimen and laser light intensities; obtains from the memory unit a laser light intensity corresponding to the depth of the observation plane; and controls the light-source unit to output the obtained laser light intensity.

5. A multiphoton-excitation observation apparatus according to claim 3, wherein the control apparatus includes a memory unit for storing, in association with each other, observation plane depths in the specimen and numbers of irradiated pulses of laser light; obtains from the memory unit a number of irradiated pulses of laser light corresponding to the depth of the observation plane; and controls the light-source unit to output the obtained number of irradiated pulses.

6. A multiphoton-excitation observation apparatus according to claim 2, further comprising an input unit for inputting contents to be stored in the memory unit.

7. A multiphoton-excitation observation apparatus according to claim 1, further comprising:
   a laser scanning unit for scanning the laser light emitted from the light-source unit;
   an objective optical system for focusing the laser light scanned by the laser scanning unit in the specimen; and
   a light-detecting device for detecting fluorescence emitted from the focal position of the laser light in the specimen,
   wherein the light-detecting device includes
      a detector for outputting a detection signal according to the incident fluorescence; and
      a detector controller for adjusting a detection sensitivity of the fluorescence in the detector according to the depth of the observation plane in the specimen.

8. A multiphoton-excitation observation apparatus according to claim 7, wherein the detection controller adjusts at least one of the sensitivity of photo-electric conversion and an integration time of the output signal in the detector.

9. A multiphoton-excitation observation apparatus according to claim 7, wherein
   the light-detecting device includes a pinhole, and
   the detection controller adjusts an opening diameter of the pin-hole.

* * * * *